US00PP36991P2

(12) United States Plant Patent
Ammerlaan

(10) Patent No.: US PP36,991 P2
(45) Date of Patent: Sep. 30, 2025

(54) ***ARISTERIA* PLANT NAMED 'OVROCKS17'**

(50) Latin Name: *xAristeria nowotnyi*
Varietal Denomination: OVROCKS17

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/831,561

(22) Filed: Apr. 17, 2025

(30) Foreign Application Priority Data

Nov. 22, 2024 (QZ) ..... PBR 2024/2739

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct x *Aristeria* plant named 'OVROCKS17' which is characterized by thin lanceolate foliage, with a transparent greyed-green mucronate tip, grown in a compact basal rosette with secondary shoots with greyed-green, serrate to dentate margins. Greyed-green to yellow-green foliage that is moderately to densely covered with greyed-green protuberances, and greyed-green spines on the top one-third of the midrib on the abaxial surface. The new variety has shown to be uniform and stable in the resulting generations from asexual propagation.

4 Drawing Sheets

Latin name of the genus and species: The Latin name of the genus and species of the novel variety disclosed herein is x *Aristeria nowotnyi. Variety denomination:*

The inventive variety of x *Aristeria* disclosed herein has been given the variety denomination 'OVROCKS17'.

CROSS REFERENCE TO RELATED APPLICATIONS

This application claims priority to the Community Plant Variety Rights application number 2024/2739, filed on Nov. 22, 2024, which is herein incorporated by reference.

BACKGROUND OF THE INVENTION

Parentage: 'OVROCKS17' is a seedling selection resulting from the controlled pollination of an unnamed *Gasteria* hybrid plant (unpatented), the seed parent, with an unnamed *Aristaloe aristata* plant (unpatented), the pollen parent. The crossing was made by the inventor in 2018 at a commercial greenhouse in Bleiswijk, the Netherlands. In early 2019, one seedling from said cross was observed to exhibit unique foliage and growth characteristics when compared to the parent plants and all other progenies. After confirming the stability of the unique characteristics first observed, the new plant was selected for commercialization and given the name, 'OVROCKS17'.

Asexual Reproduction: 'OVROCKS17' was first asexually propagated by leaf cuttings in the summer of 2019 at a greenhouse in Bleiswijk, The Netherlands. Through subsequent generations, the unique features of this cultivar are stable and reproduced true to type.

SUMMARY OF THE INVENTION

The cultivar 'OVROCKS17' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS17'. These characteristics in combination distinguish 'OVROCKS17' as a new and distinct x *Aristeria* cultivar:

1. 'OVROCKS17' exhibits thin lanceolate foliage, with a transparent greyed-green mucronate tip; and
2. 'OVROCKS17' exhibits a compact basal rosette growth habit with secondary rosettes eventually developing at the base of the primary rosette; and
3. 'OVROCKS17' exhibits greyed-green to yellow-green foliage that is moderately to densely covered with greyed-green protuberances that are randomly arranged on the adaxial leaf surface; and
4. 'OVROCKS17' exhibits succulent foliage that is densely covered with greyed- green protuberances that are irregularly arranged in transverse horizontal rows on the abaxial leaf surface along with spines on the top one-third of the midrib; and
5. 'OVROCKS17' exhibits finely serrate to dentate margins with greyed-green teeth.

BOTANICAL DESCRIPTION OF THE PLANT

Figure 1:
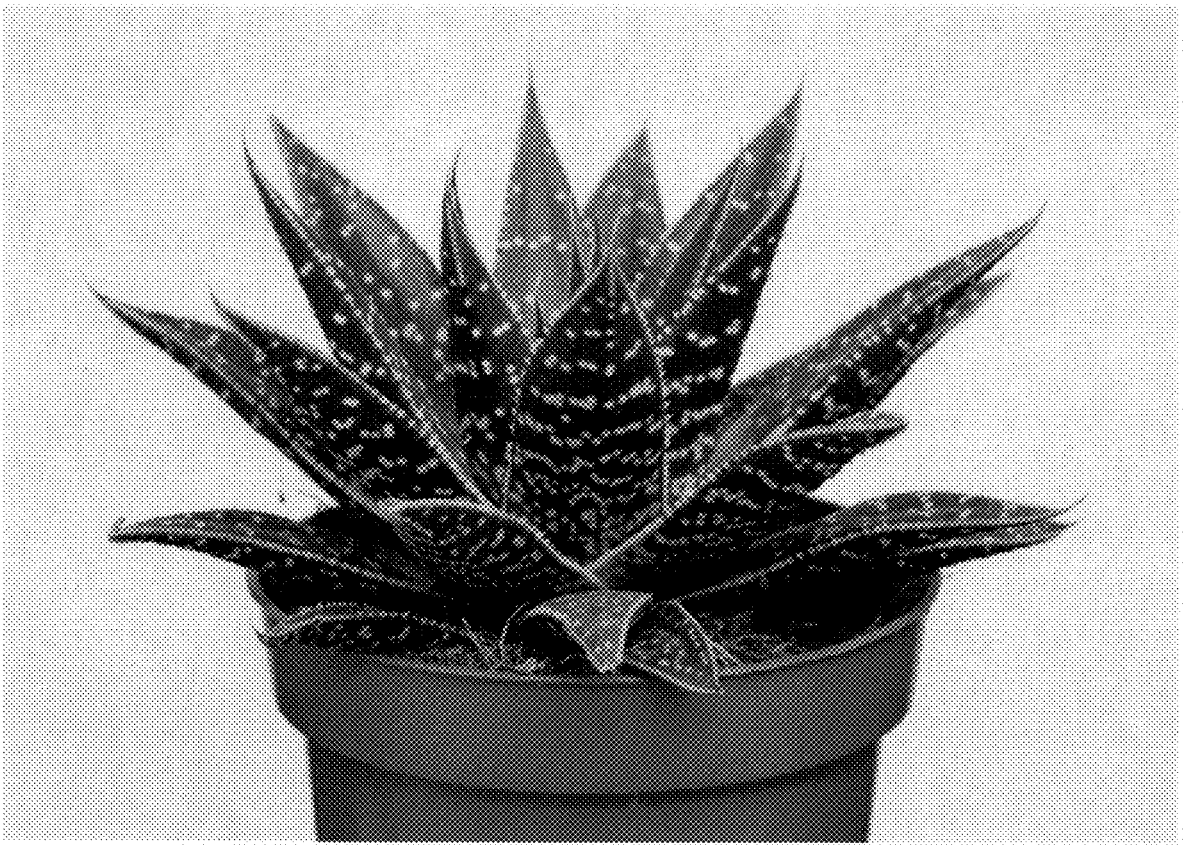
FIG. 1 illustrates, as nearly true as it is reasonably possible to make the same in color photographs of this type, an exemplary plant of 'OVROCKS17' grown in a commercial greenhouse in Bleiswijk, the Netherlands. This plant is approximately 36-month-old, shown planted in a 12 cm container.
Figure 2:
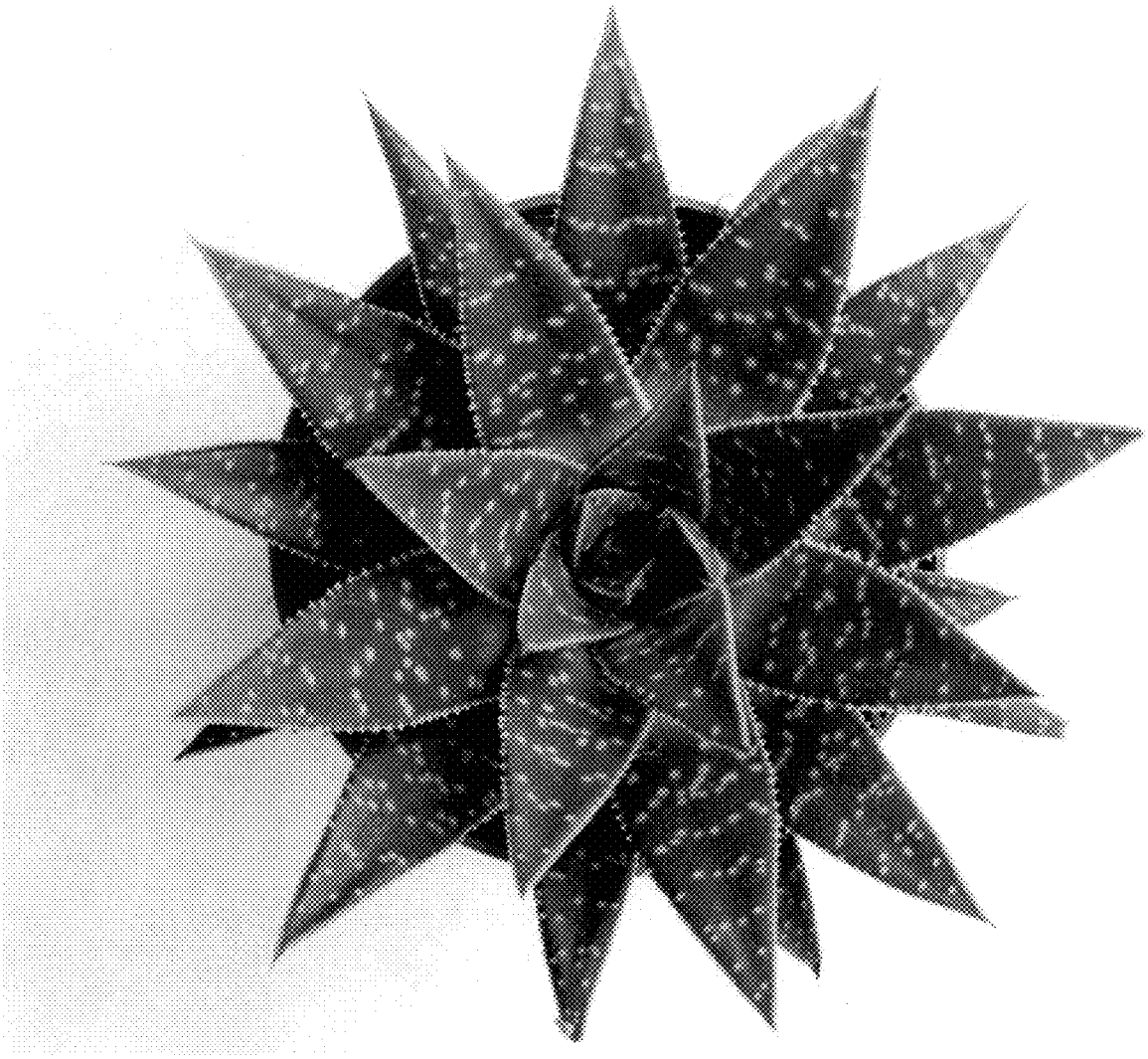
FIG. 2 illustrates, as nearly true as it is reasonably possible to make the same in color photographs of this type, the typical foliage arrangement of 'OVROCKS17'.
Figure 3:
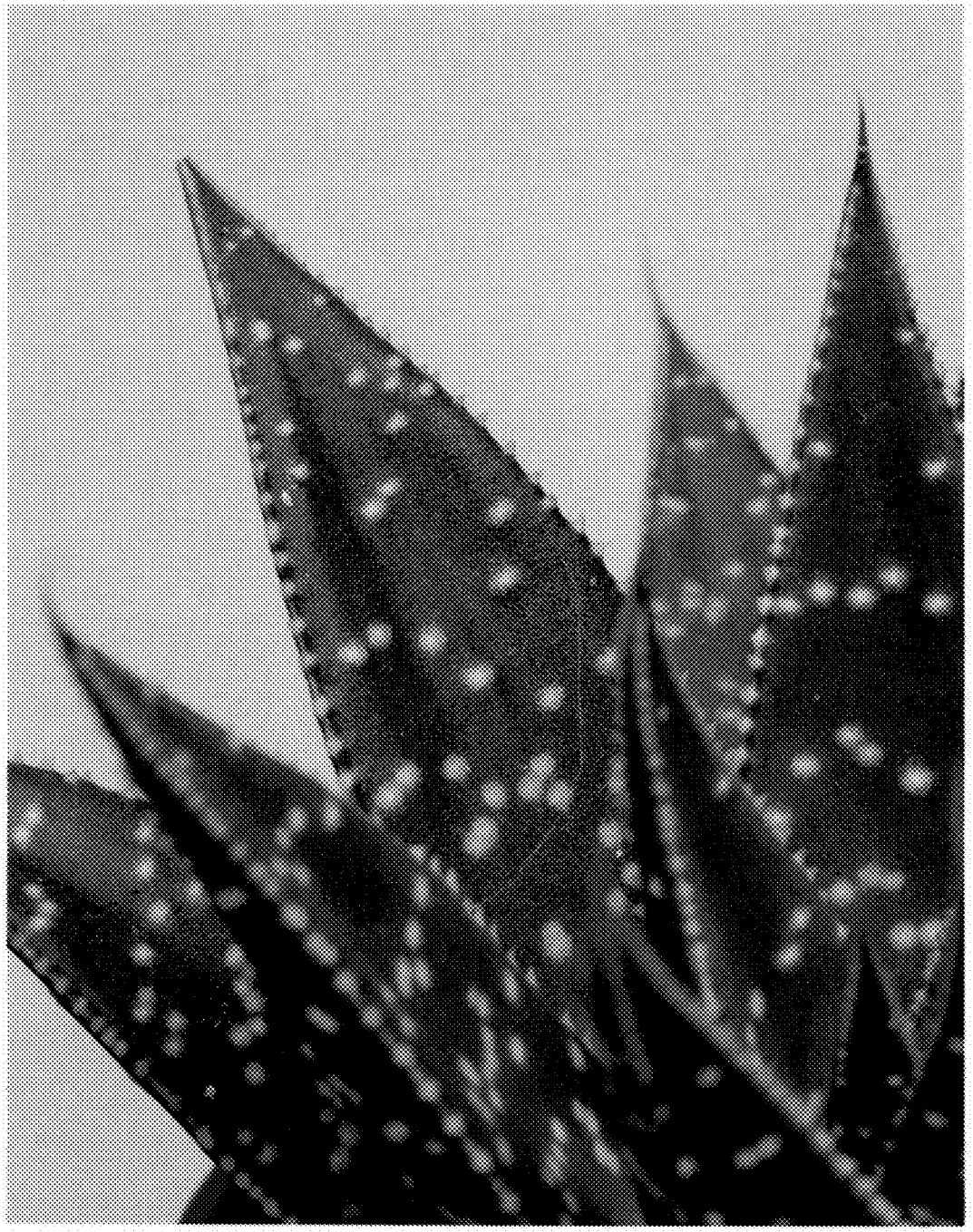
FIG. 3 illustrates, as nearly true as it is reasonably possible to make the same in color photographs of this type, the adaxial surface of the mature foliage 'OVROCKS17'.
Figure 4:
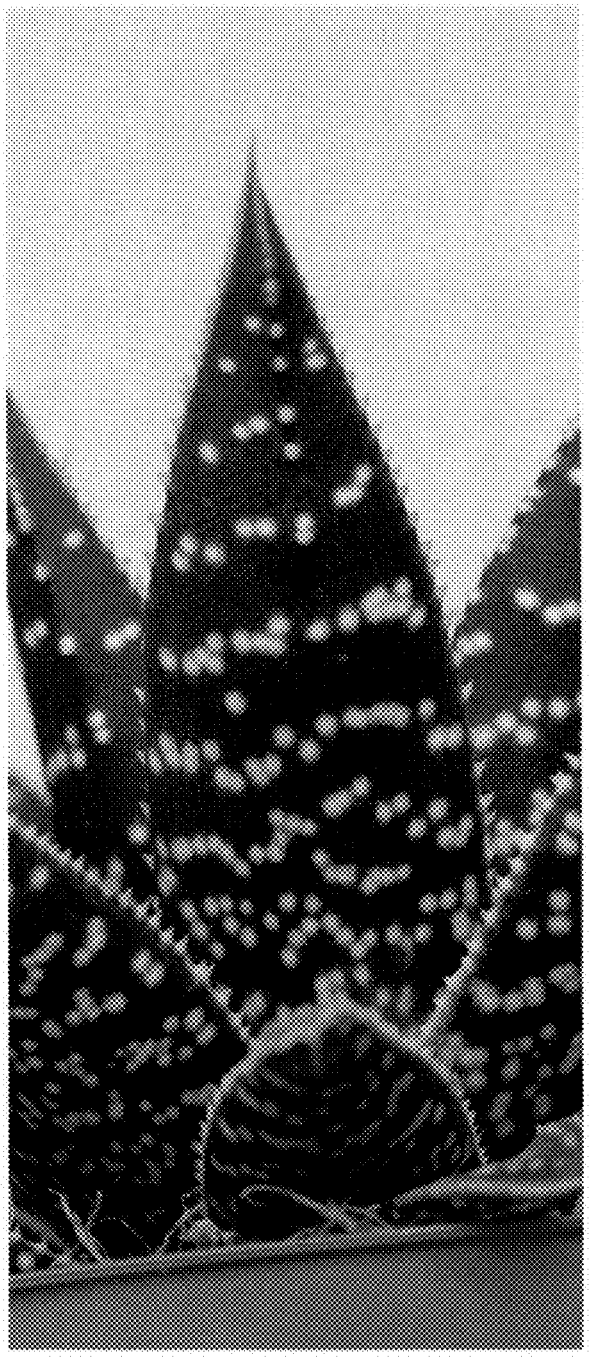
FIG. 4 illustrates, as nearly true as it is reasonably possible to make the same in color photographs of this type, the abaxial surface of the mature foliage 'OVROCKS17'.

The following observations and measurements made in November of 2024 describe averages from a sample set of six specimens of 36-month-old 'OVROCKS17' plants grown in 12 cm nursery containers at a commercial greenhouse in Bleiswijk, the Netherlands. Plants were produced using conventional greenhouse production protocols for x *Aristeria* which consisted of minimal overhead irrigation and fertilizer applications. No pest or disease control measures were utilized in production. No photoperiodic treatments or artificial light was given to the plants.

Those skilled in the art will appreciate that certain characteristics will vary with older or, conversely, with younger plants. 'OVROCKS17' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVROCKS17' and a comparison with the parent plants and closest known comparator is provided below.

Plant description:

*Growth habit*.—Succulent perennial with foliage growing in a compact basal rosette; as plants age, secondary rosettes develop at the base of the primary rosette.

*Plant form*.—Globular.

*Height from soil level to top of foliar plane*.—9.5 cm.

*Plant spread*.—Average of 17.0 cm.

*Propagation*.—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility*.—Neither resistance nor susceptibility to typical x *Aristeria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Spirally arranged in a basal rosette.

*Division*.—Simple.

*Attachment*.—Sessile.

*Quantity*.—Approximately 36 leaves per rosette.

*Shape*.—Lanceolate, succulent leaves.

*Dimensions*.—8.7 cm long, 2.8 cm wide, and 0.9 cm thick.

*Aspect*.—Very slightly concave.

*Attitude*.—Foliage is held upright at and near the center of the rosette and becomes progressively more relaxed towards the outer whorls of foliage, at an average angle of 40 degrees from horizontal; lamina is very slightly curled downward with the distal portion at and near the apex being slightly curled upward at a 60 degrees from the lamina.

*Apex*.—Narrow acute, with a soft mucronate tip.

*Base*.—Broad cuneate.

*Margin*.—Finely serrate to dentate; teeth have an average length of 0.8 cm and are colored greyed-green, nearest to RHS 192C and 192D. Margins are not undulated or lobed.

*Pubescence and texture of the adaxial surface*.—Coriaceous, and moderately covered with small, round protuberances that are irregularly arranged on the leaf surface; protuberances are approximately 0.1 cm in diameter and gradually become more raised distally from the point of attachment ultimately becoming 0.3 mm in height.

*Pubescence and texture of the abaxial surface*.—Coriaceous, and densely covered with small, round protuberances that are irregularly arranged on the leaf surface in transverse longitudinal rows; protuberances are approximately 0.15 mm in diameter and gradually become more raised distally from the point of attachment ultimately becoming 0.3 mm in height; prominent greyed-green, nearest to RHS 193B, protuberances along the top one-third of the midrib appear to be 0.5 mm.

*Luster of the adaxial surface*.—Slightly glossy.

*Luster of the abaxial surface*.—Slightly glossy.

*Color*.—Juvenile foliage, adaxial surface — Green, nearest to RHS NN137C, and fading to yellow-green towards the base, nearest to RHS 152D; the mucronate tip of the lamina is transparent greyed-green, nearest to 193A. Protuberances are colored greyed-green, nearest to RHS 193B. Juvenile foliage, abaxial surface — Green, nearest to RHS NN137C, and fading to yellow-green towards the base, nearest to RHS 151A; the mucronate tip of the lamina is transparent greyed-green, nearest to 193A. Protuberances are colored greyed-green, nearest to RHS 192A. Mature foliage, adaxial surface — In between a mixture of greyed-green and yellow-green, nearest to a blend of RHS 147A and N189A, and fading to greyed-green towards the base, nearest to RHS 191B; the mucronate tip of the lamina is transparent greyed-green, nearest to RHS 192B. Protuberances are colored greyed-green, nearest to RHS 193B. Mature foliage, abaxial surface — In between a mixture of greyed-green and yellow-green, nearest to a blend of RHS 147A and N189A and fading green towards the base, nearest to RHS 143A; the mucronate tip of the lamina is transparent greyed-green, nearest to RHS 192B. Protuberances are colored greyed-green, nearest to RHS 192A.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANTS

Plants of the new cultivar 'OVROCKS17' differ from the seed parent, an unnamed *Gasteria* hybrid plant (not patented), in the following characteristics described in Table 1 below.

TABLE 1

Comparison Between 'OVROCKS17' and The Seed Parent.

| Characteristic | 'OVROCKS17' | The Seed Parent |
|---|---|---|
| Abundance of foliage. | More abundant than the seed parent, on average 36 leaves. | Less abundant than 'OVROCKS17'. |
| Foliage aspect and arrangement. | Foliage is more concave and arranged in a more upright position, closer to vertical, than the seed parent. | Foliage is less concave than 'OVROCKS17', arranged in a relaxed, near horizonal position. |
| Foliage shape. | Thin lanceolate foliage with narrow acute apices and a mucronate tip. | Thicker and broader lanceolate succulent foliage than 'OVROCKS17' with obtuse apices. |

Plants of the new cultivar 'OVROCKS17' differ from the pollen parent, an unnamed *Aristaloe aristata* plant (not patented), in the following characteristics described in Table 2 below.

TABLE 2

Comparison Between 'OVROCKS17' and The Pollen Parent.

| Characteristic | 'OVROCKS17' | The Pollen Parent |
|---|---|---|
| General coloration of the mature foliage. | Greyed-green to yellow-green foliage. | Lighter shade of green than 'OVROCKS17'. |

TABLE 2-continued

Comparison Between 'OVROCKS17' and The Pollen Parent.

| Characteristic | 'OVROCKS17' | The Pollen Parent |
|---|---|---|
| Foliage shape and abundance. | Lanceolate succulent foliage that is thicker and broader than the pollen parent. | Lanceolate succulent foliage that is thinner than 'OVROCKS17'. |
| Abundance and attitude of foliage. | Less leaves that rest more relaxed than the pollen parent. | More leaves in a tighter compact basal rosette than 'OVROCKS17'. |

COMPARISONS WITH THE CLOSEST KNOWN COMPARATOR

Plants of the new cultivar 'OVROCKS17' differ from the closest known commercial comparator, the *Gasteria* plant called 'D Blue Moon' (Community Plant Variety Rights application number 2023/1913) in the following characteristics described in Table 3 below.

TABLE 3

Comparison Between 'OVROCKS17' and 'D Blue Moon'

| Characteristic | 'OVROCKS17' | 'D BLUE MOON' |
|---|---|---|
| General thickness of foliage. | Lanceolate succulent foliage that is thinner on average than 'D Blue Moon'. | Ovate succulent foliage that is thicker on average than 'OVROCKS17'. |
| Leaf margins. | 'OVROCKS17' has an abundance of prominent greyed-green finely serrate to dentate teeth which are evenly distributed along the leaf margins. | 'D Blue Moon' has less prominent, smaller, serrate margins when compared to 'OVROCKS17'. |
| Abundance of secondary basal rosettes. | 36 leaves per rosette with less secondary basal rosettes than 'D Blue Moon'. | More leaves per rosette with more secondary basal rosettes than 'OVROCKS17'. |
| Prominence of leaf protuberances. | Less prominent than 'D Blue Moon'. | More prominent than 'OVROCKS17'. |

That which is claimed is:

1. A new and distinct variety of x *Aristeria* plant named 'OVROCKS17', substantially as described and illustrated herein.

* * * * *